United States Patent
Huijbregts-Doorduin et al.

(10) Patent No.: US 10,829,782 B2
(45) Date of Patent: Nov. 10, 2020

(54) **QTL CONTRIBUTING TO WHITEFLY RESISTANCE IN *CUCUMIS MELO***

(71) Applicant: RIJK ZWAAN ZAADTEELT EN ZAADHANDEL B.V., De Lier (NL)

(72) Inventors: Lena Johanna Huijbregts-Doorduin, De Lier (NL); Magdalena Barbara Lastdrager, De Lier (NL); Albertus Cornelius Maria Van Den Ende, De Lier (NL); Johanna Evertje Van Elven, De Lier (NL); Ram Kumar Basnet, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 0 days.

(21) Appl. No.: 16/293,769

(22) Filed: Mar. 6, 2019

(65) Prior Publication Data
US 2019/0225984 A1 Jul. 25, 2019

Related U.S. Application Data

(63) Continuation-in-part of application No. PCT/EP2017/073177, filed on Sep. 14, 2017.

(30) Foreign Application Priority Data

Sep. 16, 2016 (WO) .................. PCT/EP2016/071999

(51) Int. Cl.
*C12N 15/82* (2006.01)
*C12Q 1/68* (2018.01)
*A01H 5/08* (2018.01)
*C12Q 1/6895* (2018.01)
*A01H 1/04* (2006.01)
*C12Q 1/6869* (2018.01)

(52) U.S. Cl.
CPC .......... *C12N 15/8286* (2013.01); *A01H 1/04* (2013.01); *A01H 5/08* (2013.01); *C12Q 1/6869* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

FOREIGN PATENT DOCUMENTS

WO 2015/177206 A1 11/2015

OTHER PUBLICATIONS

N. Boissot, et al., Mapping and Validation of QTLs for Resistance to Aphids and Whiteflies in Melon, Theor Appl. Genet (2010) 12:9-20.
Tong-Xian Liu, Response of Four Melon Varieties to Silverleaf Whitefly (*Homoptera: Aleyrodidae*) Under Laboratory and Field Conditions, Subtropical Plant Science (2003) 55:27-31.
James D. McCreight, et al., Silverleaf Whitefly Resistance Strategies in Melon, Cucurbitaceae '98 (Jan. 1, 1998) p. 113-117.
Aurora Diaz, et al., A Consensus Linkage Map for Molecular Markers and Quantitative Trait Loci Associated with Economically Important Traits in Melon, BMC Plant Biology (2011) 11:111.
Wim Deleu, et al., A Set of EST-SNPs for Map Saturation and Cultivar Identification in Melon, BMC Plant Biology (Jul. 15, 2009) 9:90.
Database EMBL Accession No. LN713258, Cumis Melo Genomic Chromosome, chr_4 (Dec. 16, 2014).
Javier M. Obando-Ulloa, et al., Identification of QTLs Related to Sugar and Organic Acid Composition in Melon Using Near-Isogenic Lines, Scientia Horticulturae (2009) 121:425-433.
R. Harel-Beja, et al., A Genetic Map of Melon Highly Enriched with Fruit Quality QTLs and EST Markers, Including Sugar and Carotenoid Metabolism Genes, Theor Appl Genet (2010) 121:511-533.
Corrected International Search Report dated May 2, 2018 issued in International Application No. PCT/EP2017/073177.

*Primary Examiner* — Medina A Ibrahim
(74) *Attorney, Agent, or Firm* — Duane Morris LLP; Thomas J. Kowalski; Deborah L. Lu

(57) ABSTRACT

The present invention relates to a *Cucumis melo* plant which carries QTL1 in its genome that leads to resistance against the *Bemisia tabaci* species complex, which QTL1 is located between flanking marker sequences SEQ ID No. 1 and SEQ ID No. 2 and can be identified by and is in particular linked to one or more markers selected from the group consisting of SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, and SEQ ID No. 12, or combinations thereof. In a further embodiment, the *Cucumis melo* plant further comprises another *Bemisia* resistance conferring QTL, which combination of QTLs leads to an improved level of resistance to the *Bemisia tabaci* species complex when compared to a plant in which only the other QTL is present.

12 Claims, 5 Drawing Sheets

Specification includes a Sequence Listing.

Fig. 1

Bemisia adult survival in clipcages

Fig. 5

SNP marker sequences

SEQ ID No. 1 with SNP A or the alternative G on position 101 is flanking the QTL1 region
CAGAAATATCTTTCTCGCTGGCTTGTGTAATAACTTGTTTCAACCGATCTTTTGAAGCCTAAATGAATAATTAGG
GAAGTGGGAAATAGTTGAAAAAACAAACGAAACCAAAACTCATATAGTGAATACAGAATTAGATCAGGAAAA
TGTTGCTGCAGTCTCACTTTTCTGCCATGYGAKTCTATGAAACATTTTTAATGG

SEQ ID No. 2 with SNP G or the alternative A on position 101 is flanking the QTL1 region
TGCTGGACGTGAGGTTTCCATGARTAAGRTTCTCCTCTGTGTGGAGGTAGTTCAAGCCTTGCGWGATTCCGAT
CGCWATTTTCATCCTTGTTGCCCAATCGACCGTGGTTTCTGGCCCACGAGCTGCATACAGTAAAACAAAAGTAA
GTATATGAGTTAYGAGTATAGYTTAACTAGATCAATAACCTCTTTCATAAGTAG

SEQ ID No. 3 - SNP G on position 101 is related to the presence of QTL 1
ACAGACCCATCCATGATGTGAAAATACTGCGGGCATCAGTTAAAGACTAAAGCTTTTCAGTTATTGACTTTTGA
CACACTCGTTGTTGTATCTCAACACTGTATGCAGCAATAAAAACCACGTTGTGTGTTTSATGACAGAAGGAAGG
AAAGGAAAWGAAAATTTTCCATGTTAGTTAGGCGAAGAAAGAGGAGGGAAAAG

SEQ ID No. 4 - SNP G on position 101 is related to the presence of QTL 1
CTTTGGACGACGGAGATCGTCAGCCAGAAGGAGAGAACAGAGAGGTCACAGAGCAGCCGGAGATTCCGCCG
GATTTTCCACCGGAATCATTTTGGCTCTCGAAGGATGCAGAGTTCGATTGGTTAGATCAAAACGCTTTTTACGA
GAGGAAAGATTCGACGAAAGGGAGTTCGAATTCAACGAACTTGAATCCTACTGTGA

SEQ ID No. 5 - SNP T on position 101 is related to the presence of QTL 1
TTGGGGGGAAAYAGTGAGTGTACGAYCAAAGAATCAAAAAGGCTTAAACAGACAAAATGTTTGAAATGGGAC
CCAATTGAAATCTGACCCTTGATTGAGATGGAGAAGATCAACGGATGGGGTTTGTTCACACATGGAGAAATAA
TTCCCACTTTCCACAGTCAAAAAAGGTCGACCACCACCGCCACGGTTGGAGCTGGA

SEQ ID No. 6 - SNP C on position 101 is related to the presence of QTL 1
TAAGGCCAAAGGAGTTGATACTATCGCTTGTATTTCwGTCAATGATGCCTTTGTGATGAAGGCGTGGAAGGAT
AACCTTAATATCAAGGATGAGGTTCTGCTRCTGTCTGATGGGAATGGGGATTTCACTAGGGCTATTGGGTGCG
AGCTGGATTTGAGCGACAAGCCTGTTGGAYTGGGTGTTAGGTCGAGACGTTATGC

SEQ ID No. 7 - SNP G on position 101 is related to the presence of QTL 1
AGAGAAACRATAGTTAAGTACCTATTGCCTTCTTCAACTCCTCGAGGTATKTAGGCTCTAACCCATCGAATGAA
TTCATAATAAAACCATAAGAAGCACTGTCAGCTTTAGCCATTTGATTCCCCCACTCCAAGAACAYAGGATCCAA
AGTAAAGATAAGTTGAGACTTGGTAACTTGAATYGRATCAGGAAAATTAGGGA

SEQ ID No. 8 - SNP C on position 101 is related to the presence of QTL 1
AGTGTGATTGACAGAAAAGTGTAGCAATAGAACTGGTAAAGAATCGCAGTGCGAGAGTAGAAGGAAGAAGT
TGAACCTAGAGCGGTGCGAAGGCCATCRACGTCGCCRAGCTGGGAGGCGGWAGCTAGGGGGCGGAGGTGA
GGGGGCGTATCGGAATCGAATTCAATAACACCGTCCTCTTCAAAGAGAGCATTGTCTTCC

SEQ ID No. 9 - SNP A on position 101 is related to the presence of QTL 1
ACTTATTACAGGAACTCGATGGGAGATCACTAAGGGTAAACTATGGACCTCCACCGAAAAGGGACGATTCCCC
TTTCAGAGGTTCTAGAAATGCTTCAAGATTTGACAACCGCAATCGGGTCCATGTGAGTAACCTTGCTTGGGGT
GTTGACGATCTTACACTTGAGAACTTGTTTAGGGAACASGGAAATGTTTTGGAGG

Fig. 5 (continued)

SEQ ID No. 10 - SNP G on position 101 is related to the presence of QTL 1
TCGAAAATTCAACCCAAAAATTAATAAAAGKAGAACAAAATCCTTACTCTGCACGCAGAACCATATGTTGGGG
CAACGGGCCCAAAACCTTCTCCATCATGGCAAGATGCTCCAAGTTCTCGTGCGTTTGAAAAAGTGCCTCACCCT
GCTCATCAAACAAAAGAAAATAACAAAATGGAAAGGTTAAGAAAATCCAKAACC

SEQ ID No. 11 - SNP G on position 101 is related to the presence of QTL 1
ACGATGCTGAGTAAAACCAGAGGGTGAACTACAACCTTCTCAACTGGCCTCGATGAAATTTGCTGCGTCTTGAT
CACATCCATGGCGGAATTTTTGCAGTGTATCAGAGTTGAATCGAATTGGCGCTTCCGTGCTAARGGCTAAACCC
ACTTAGAAATGGAGCAGCTGCTTATTAAGCCCYTTTTCTTTGAGGGGTTTTCT

SEQ ID No. 12 - SNP T on position 101 is related to the presence of QTL 1
CGAGCTGGGTTGGAATGTAYGTATTGAACACGTTCGTGGTGGCRTGGGTTCTTGTGGTTGGGTTTGGGTTTGG
AGGATGGGCTAGTATGACGAACTTTGTTAGGCAAGTAGACACCTTCGGACTTTTCGCAAAGTGCTATCAGTGC
AAGGGTCCCCCGTTRCCTGCGAKGGCTCCAACTGCTCATCATTAAACTCTGGGCA

QTL CONTRIBUTING TO WHITEFLY RESISTANCE IN CUCUMIS MELO

RELATED APPLICATIONS AND INCORPORATION BY REFERENCE

This application is a continuation-in-part application of international patent application Serial No. PCT/EP2017/073177 filed 14 Sep. 2017, which published as PCT Publication No. WO 2018/050765 on 22 Mar. 2018, which claims benefit of international patent application Serial No. PCT/EP2016/071999 filed 16 Sep. 2016.

The foregoing applications, and all documents cited therein or during their prosecution ("appin cited documents") and all documents cited or referenced in the appin cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy is named 00418Sequence_Listing.txt and is 4.58 Kbytes in size.

FIELD OF THE INVENTION

The present invention relates to a *Cucumis melo* plant that is resistant to *Bemisia tabaci*. The invention further relates to markers linked to the resistance and the use of markers to identify resistant plants. The invention also relates to the seeds and progeny of such plants and to propagation material for obtaining such plants.

BACKGROUND OF THE INVENTION

Cultivation of melon (*Cucumis melo*) is typically done in unprotected or semi-protected environments, such as open field or in tunnels. The crop is therefore vulnerable to a variation of biotic and abiotic stress factors that are influencing growth, development, and naturally yield.

Amongst the pests and diseases of melon, whitefly is one of the most prolific and difficult to control due to their fast development, high fertility, and wide dispersion capacity. The whitefly, *Bemisia tabaci* (Gennadius) (Hemiptera: Aleyrodidae), is considered a cryptic species complex comprising a number of morphologically indistinguishable, but genetically distinct species or biotypes. The whitefly is commonly, and sometimes interchangeably, referred to as the tobacco whitefly, sweet potato whitefly, or silverleaf whitefly. The most widespread and invasive biotypes within the *B. tabaci* species complex are biotype B (also referred to as the silverleaf whitefly, or *Bemisia argentifolii*) and biotype Q.

Members of the *B. tabaci* species complex, such as biotype B and Q, are considered a major insect pest of significant economic importance, because they affect a diverse range of agricultural crops including ornamental and vegetable plants. Amongst vegetable crops, very susceptible hosts include melons, cucumbers, beans, eggplant, cabbage, peppers, squash, and tomatoes.

The whitefly life cycle ranges from 2-3 weeks to up to 2 months, depending on temperature and environmental conditions. Whiteflies lay their eggs on the undersurface of leaves where they remain attached until they hatch. Upon hatching, the first nymph or instar (crawler) moves from the egg site to a suitable feeding location on the lower leaf surface. The nymph becomes sessile throughout the remaining nymphal stages up to puparium. After the adult whitefly emerges from the pupal stage, it can start to mate 12-20 hours following emergence, and will continue to mate several times throughout adulthood. Females can lay between 50-400 eggs, resulting in large whitefly populations only after a few generations.

Whiteflies cause both direct and indirect damage to infested plants. Direct damage is caused through feeding. The whitefly uses its piercing and sucking stylet to inject enzymes into the plant, ultimately enabling it to extract phloem (carbohydrates and amino acids). Feeding by large numbers of whiteflies reduces plant vigour and overall plant health. Additional damage is caused by their honeydew excretions, which acts as a substrate for sooty mold. Honeydew and sooty mold not only interfere with photosynthesis but can also reduce the quantity, quality and marketability of affected fruits, vegetables, and ornamentals.

In addition to direct damage, whiteflies are known to vector highly devastating plant viruses, such as viruses belonging to the genera begomoviruses, ipomoviruses, criniviruses, carlaviruses, and closteroviruses. Common damage symptoms caused directly and indirectly by whiteflies are for example stem bleaching, chlorotic spots, stippling, leaf yellowing, silver leaf, leaf curling, yellow veining, leaf drop, or plant death.

Whitefly control has proven to be difficult and complex. Traditional means of whitefly control in the field and glasshouse by insecticides have, in some instances, led to insecticide resistance. Biological control agents, such as natural predators, parasitoids and pathogens of the whitefly have only been moderately effective in some crops in controlling whitefly infestations. However, no single control treatment has proven to be an effective long term control method against whiteflies.

In melon, whiteflies are still largely managed by frequent insecticide applications. The environmental impact of this practice however, is considered to be high risk as a long term solution. More sustainable management methods, such as developing melon genotypes resistant to *B. tabaci*, are therefore sought after.

Several *C. melo* sources possessing a certain level of whitefly resistance have been identified. The Korean accession PI161375 has come up as a source having a certain level of field resistance in various studies. Also the accession 90625, which is also known as PI313970, and PI164723 have surfaced repeatedly as *C. melo* material having a level of field resistance. These accessions also have value as sources for other resistances, as they for example also are found to have aphid resistance, and they have been identified as sources for virus resistance in *C. melo*. It was however also found that none of these sources appear to have a sufficient resistance level to *Bemisia* whitefly, and that higher levels of resistance are needed for a good genetic control of whitefly in *C. melo*.

In patent application WO2015177206 a QTL on chromosome 11 is identified as a QTL which is conferring resistance to the whitefly *Bemisia tabaci* biotype B. A large number of SNP markers to identify this QTL is given, spanning a region of about 20 to 40 cM depending on which population is considered. The resistant version of most of the SNP markers of WO2015177206 can be located on the public melon genome sequence that was published in 2012 (Garcia-Mas et al. PNAS Vol. 109(29):11872-11877, 2012). The resistant source PI161375 was used as a parent in the development of the line DHL92, which is the basis of this public melon genome sequence.

The level of resistance of prior art resistant sources such as PI313970 and PI161375 was assessed to require improvement, as the level is not sufficient to develop commercial melon varieties that can be indicated as whitefly resistant. This follows also from the fact that resistant material was already identified as early as 2003, but no commercial *C. melo* varieties claiming to be whitefly resistant are marketed yet. Further research was therefore carried out internally with other *C. melo* sources that were not publicly known for their *Bemisia* resistance. In this process a QTL that contributes to resistance to the *Bemisia tabaci* species complex was identified. Both biotype B, also referred to as the silverleaf whitefly, as well as biotype Q belong to the *Bemisia tabaci* species complex. Cultivated material that was resistant to this complex, comprising said QTL, indicated as QTL1, was internally developed. QTL1 was also introgressed in parental breeding lines, that are used for increasing resistance in cultivated *C. melo* varieties.

Citation or identification of any document in this application is not an admission that such document is available as prior art to the present invention.

SUMMARY OF THE INVENTION

It is an object of the present invention to provide a *Cucumis melo* plant that may comprise one or more QTLs which confer resistance against the *Bemisia tabaci* species complex.

The invention thus relates to a *Cucumis melo* plant which carries QTL1 in its genome that leads to resistance against the *Bemisia tabaci* species complex, which QTL1 is located on chromosome 4 between flanking marker sequences SEQ ID No. 1 and SEQ ID No. 2. The *C. melo* plant of the invention is a cultivated melon plant and preferably an agronomically elite *C. melo* plant.

The presence of the resistance-conferring QTL1 can be identified by a number of markers that are present between the flanking marker sequences and that are linked to the QTL1 region that confers resistance to the *Bemisia tabaci* species complex. The actual markers that are informative can depend on the background of the population that is observed, since polymorphisms can vary between genotypes. A marker that can identify QTL1 is a marker that is linked to QTL1 in a certain population.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSIT

Seeds of *Cucumis melo* 15R. 15347000 that comprise QTL1 in homozygous form were deposited with NCIMB Ltd, Ferguson Building, Craibstone Estate, Bucksburn, Aberdeen AB21 9YA, UK on 13 May 2016 under deposit accession number NCIMB 42572.

The Deposit with NCIMB Ltd., under deposit accession number 42572 were made pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, given by way of example, but not intended to limit the invention solely to the specific embodiments described, may best be understood in conjunction with the accompanying drawings.

FIG. 1: adult survival rate of *Bemisia* whitefly in a no-choice, or non-preference, experiment.

FIG. 5: sequences of SEQ ID Nos. 1-12. The SNP related to the presence of QTL1 and the resistant genotype is underlined and indicated in bold.

DETAILED DESCRIPTION OF THE INVENTION

Figure 2:
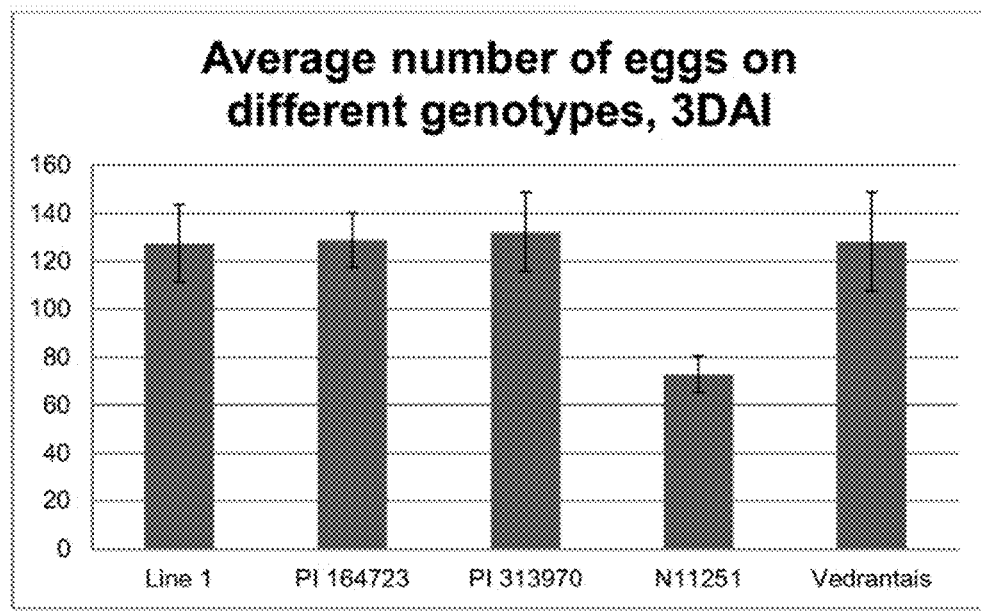
FIG. 2: differences in oviposition of *Bemisia* whitefly on different *C. melo* accessions, indicated as the number of eggs per plant from an average of six plants.

As used herein, resistance to the 'Bemisia tabaci species complex' is resistance to biotype B, also referred to as the silverleaf whitefly or Bemisia argentifolii, and resistance to biotype Q.

As used herein, resistance to the Bemisia tabaci species complex is a resistance based on both antibiosis as well as antixenosis. Antixenosis resistance affects the behavior of an insect pest, and is also expressed as non-preference of the insect for a resistant plant when compared with a susceptible plant. This means that when given the choice, the Bemisia whitefly has less preference for a plant having antixenosis resistance, as compared to a plant that does not have the resistance QTL (Example 1). In addition, non-choice tests showed that once a whitefly is forced to feed and reproduce on a plant which may comprise the resistance of the invention, survival and reproduction is reduced as compared to a plant lacking said resistance (Example 2). This mechanism is based on antibiosis, which affects the biology of the insect and generally results in increased mortality and/or reduced longevity and reproduction of the insect. The result is that pest abundance and subsequent damage on a plant having antibiosis resistance is reduced compared to that which would have occurred if the insect was on a susceptible crop variety. The combination of antibiosis and antixenosis leads to an increased level of field resistance, which is a reduction in pest incidence and/or a reduction in the symptoms caused by the presence of the pest.

The resistance of the present invention caused by the presence of QTL 1 does not inherit in a complete dominant fashion. This means that the highest level of resistance is obtained when QTL1 is present homozygously. The heterozygous presence of QTL 1 may also give a certain level of resistance, but this resistance is lower than in a plant were QTL1 is present homozygously. The resistance conferred by QTL1 of the present invention therefore has a recessive or intermediate inheritance.

QTL mapping studies were performed to identify the genetic region for the cause of this trait. In these studies a QTL, designated QTL1, was identified on chromosome 4. Table 1 shows the two flanking markers having SEQ ID No. 1 and SEQ ID No. 2 that indicate the positions on chromosome 4 between which QTL1 is located. When the sequences of these markers are positioned on the publicly available genome sequence for Cucumis melo which is based on the C. melo line DHL92, the physical position to which the SNP polymorphism in said marker sequence corresponds is also indicated in Table 1. The position of QTL1 is therefore also derivable from this public map and is relative to said physical positions. The C. melo genome sequence based on DHL92 that is used is the genome as published in Garcia-Mas et al. PNAS Vol. 109(29):11872-11877, 2012. Data of this genome can for example be accessed at melonomics.net. This C. melo genome based on DHL92 is the reference for 'the public C. melo genome' as used herein.

TABLE 1 polymorphisms and positions of the SNP markers

| SEQ ID No. | Genetic position in population (Vedrantais x N11251) F2 | Physical position of the SNP (based on the public DHL92 genome) | Polymorphism | Position of the SNP in the sequence of FIG. 5 |
|---|---|---|---|---|
| SEQ ID No. 1 | 24.4 cM | 30.112.113 | [G/A] | 101 |
| SEQ ID No. 2 | 0.0 cM | 32.828.273 | [A/G] | 101 |
| SEQ ID No. 3 | 22.3 cM | 30.513.631 | [T/G] | 101 |
| SEQ ID No. 4 | 21.9 cM | 30.638.514 | [C/G] | 101 |
| SEQ ID No. 5 | 19.5 cM | 30.874.879 | [G/T] | 101 |
| SEQ ID No. 6 | | 31.039.319 | [T/C] | 101 |
| SEQ ID No. 7 | | 31.254.936 | [A/G] | 101 |
| SEQ ID No. 8 | 16.1 cM | 31.314.600 | [T/C] | 101 |
| SEQ ID No. 9 | 14.9 cM | 31.559.189 | [C/A] | 101 |
| SEQ ID No. 10 | | 31.960.600 | [T/G] | 101 |
| SEQ ID No. 11 | 2.1 cM | 32.518.833 | [A/G] | 101 |
| SEQ ID No. 12 | 0.8 cM | 32.558.988 | [C/T] | 101 |

Further genotyping resulted in the mapping of various SNP markers that can be used for determining the presence of QTL1 in the genome of a plant, which SNP markers are represented by SEQ ID Nos. 1-12. The sequences of SEQ ID Nos. 1-12 that are related to the presence of QTL1 can be found in FIG. 5.

In one embodiment QTL1 is linked to one or more markers selected from the group consisting of SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11 and SEQ ID No. 12, or combinations thereof.

QTL1 is in particular located between SEQ ID No. 6 and SEQ ID No. 2. QTL1 which is located between SEQ ID No. 6 and SEQ ID No. 2 can be identified by one or more markers selected from the group consisting of SEQ ID No. 7, SEQ ID No. 8, SEQ ID No. 9, SEQ ID No. 10, SEQ ID No. 11 and SEQ ID No. 12, or combinations thereof.

In one embodiment QTL1 is linked to the marker having SEQ ID No. 11.

According to a further aspect thereof, the invention relates to a C. melo plant which may comprise a QTL1 that contributes to resistance to the Bemisia tabaci species complex, which QTL1 is as comprised in a C. melo plant representative seed of which was deposited with the NCIMB under deposit number NCIMB 42572. Such a plant of the invention therefore has the same QTL1 as the QTL1 that is present in the genome of seeds of deposit NCIMB 42572.

The QTL1 that leads to resistance to the Bemisia tabaci species complex is suitably introgressed from a C. melo plant which may comprise said QTL1, representative seed of which was deposited with the NCIMB under deposit number NCIMB 42572, or from a progeny plant thereof.

In NCIMB 42572 QTL1 is located on chromosome 4 between marker sequences SEQ ID No. 1 and SEQ ID No. 2.

In NCIMB 42572 QTL1 is linked to one or more of the markers selected from the group consisting of SEQ ID No. 3, SEQ ID No. 4, SEQ ID No. 5, SEQ ID No. 6, SEQ ID No. 8, SEQ ID No. 9, SEQ ID No. 10, SEQ ID No. 11 and SEQ ID No. 12, or combinations thereof. In a preferred embodiment in NCIMB 42572 QTL1 is linked to one or more of the markers having SEQ ID No. 6, SEQ ID No. 8, SEQ ID No. 9, SEQ ID No. 10, SEQ ID No. 11, SEQ ID No. 12, or to combinations thereof. In NCIMB 42572 QTL1 is linked to the marker having SEQ ID No. 11.

In one embodiment the invention relates to a *C. melo* plant which may comprise QTL1 as found in NCIMB 42572 which is located on chromosome 4 between marker sequences SEQ ID No. 1 and SEQ ID No. 2.

In one embodiment the invention relates to a *C. melo* plant which may comprise QTL1 as found in NCIMB 42572 which is located on chromosome 4 and is linked to at least one of the markers having SEQ ID No. 3, SEQ ID No. 4, SEQ ID No. 5, SEQ ID No. 6, SEQ ID No. 8, SEQ ID No. 9, SEQ ID No. 10, SEQ ID No. 11, SEQ ID No. 12, or to combinations thereof.

In a preferred embodiment the invention relates to a *C. melo* plant which may comprise QTL1 as found in NCIMB 42572 which is located on chromosome 4 and is linked to at least one of the markers having SEQ ID No. 6, SEQ ID No. 8, SEQ ID No. 9, SEQ ID No. 10, SEQ ID No. 11, SEQ ID No. 12, or to any combination thereof.

In a preferred embodiment the invention relates to a *C. melo* plant which may comprise QTL1 as found in NCIMB 42572 which is located on chromosome 4 and is linked to the marker having SEQ ID No. 11.

When a marker is said herein to be linked to QTL1 it means that the marker is physically linked to this QTL1 and is thus also physically located on chromosome 4.

Introgression of QTL1 as used herein means introduction of QTL1 from a donor plant which may comprise said QTL1 into a recipient plant not carrying said QTL1 by standard breeding techniques, wherein selection can be done phenotypically by means of observation of the resistance to the *Bemisia tabaci* species complex, or selection can be done with the use of markers through marker assisted breeding, or combinations of these. Selection is started in the F1 or any further generation from a cross between the recipient plant and the donor plant, suitably by using markers as identified herein. The skilled person is however familiar with creating and using new molecular markers that can identify or are linked to the trait of resistance to the *Bemisia tabaci* species complex. Development and use of such markers for identification and selection of plants of the invention is also part of the invention.

In one embodiment the QTL1 of the invention is introgressed in a *Cucumis melo* plant which may comprise another *Bemisia* resistance conferring QTL, which combination of QTLs leads to an improved level of resistance to the *Bemisia tabaci* species complex when compared to a plant in which only the other QTL is present.

In one embodiment the QTL1 of the invention is introgressed in a *C. melo* plant which may comprise a QTL on chromosome 11 as is present in PI161375 and/or PI313970. Internal research identified in PI161375 and PI313970 the presence of a QTL on chromosome 11. By adding QTL1 of the invention, the resistance level of said *C. melo* material against the *Bemisia tabaci* species complex is then increased or made more sustainable through a combination of different resistance mechanisms or different genetic causes for resistance, as compared to when only the said QTL on chromosome 11 is present, or when only QTL1 of the invention is present.

In one embodiment the invention relates to a *Cucumis melo* plant which may comprise QTL1 of the invention, which further may comprise another *Bemisia* resistance conferring QTL, which combination of QTLs leads to an improved level of resistance to the *Bemisia tabaci* species complex when compared to a plant in which only the other QTL is present. The other *Bemisia* resistance conferring QTL is suitably a QTL on chromosome 11 as is present in PI161375 and/or PI313970, but can also be another *Bemisia* resistance conferring QTL.

The invention also relates to a *C. melo* fruit or a *C. melo* plant carrying only one allele of QTL1. Such plant or fruit can be used as a source for the development of a plant which may comprise two alleles of QTL1.

The term "an allele of QTL1" as used herein is the version of QTL1 that leads to resistance to the *Bemisia tabaci* species complex. The wild type allele does not lead to resistance. The presence of an allele of QTL1 can suitably be identified using a marker as described herein. The presence of two alleles means that the resistant version of QTL1 is present homozygously. In a preferred embodiment QTL1 is present in homozygous form.

The invention also relates to the use of a plant of the invention that may comprise QTL1 as a source of propagating material.

The invention also relates to the use of a plant of the invention that may comprise QTL1 in plant breeding.

The invention furthermore relates to a cell of a plant as claimed. Such cell may be either in isolated form or may be part of the complete plant or parts thereof and then still constitutes a cell of the invention because such a cell harbours the genetic information that leads to resistance to the *Bemisia tabaci* species complex of a *C. melo* plant. Each cell of a plant of the invention carries the genetic information that leads to resistance to the *Bemisia tabaci* species complex. Such a cell of the invention may also be a regenerable cell that can be used to regenerate a new plant of the invention. The presence of genetic information as used herein is the presence of QTL1 as defined herein.

The invention also relates to tissue of a plant as claimed. The tissue can be undifferentiated tissue or already differentiated tissue. Undifferentiated tissues are for example stem tips, anthers, petals, pollen, and can be used in micropropagation to obtain new plantlets that are grown into new plants of the invention. The tissue can also be grown from a cell of the invention.

The invention according to a further aspect thereof relates to seed, wherein the plant that can be grown from the seed is a plant of the invention which may comprise QTL1 which leads to resistance to the *Bemisia tabaci* species complex in a *C. melo* plant. The invention also relates to seeds from a plant as claimed. The seeds harbour the QTL1 that, when a plant is grown from the seed, makes this plant a plant of the invention.

The invention also relates to progeny of the plants, cells, tissues and seeds of the invention, which progeny may comprise QTL1 that leads to resistance to the *Bemisia tabaci* species complex. Such progeny can in itself be plants, cells, tissues, or seeds.

As used herein the word 'progeny' is intended to mean the first and all further descendants from a cross with a plant of the invention that may comprise the QTL1 that leads to resistance to the *Bemisia tabaci* species complex.

'Progeny' also encompasses plants that carry QTL1 of the invention and optionally, when QTL1 is present homozygously, have the trait of the invention, and are obtained from other plants, or progeny of plants, of the invention by vegetative propagation or multiplication. Progeny of the invention may comprise QTL1 and suitably shows resistance to the *Bemisia tabaci* species complex.

The term "trait of the invention" as used herein is intended to refer to the trait of resistance to the *Bemisia tabaci* species complex.

The invention further relates to parts of a claimed plant that are suitable for sexual reproduction. Such parts are for example selected from the group consisting of microspores, pollen, ovaries, ovules, embryo sacs, and egg cells. In addition, the invention relates to parts of a claimed plant that are suitable for vegetative reproduction, which are in particular cuttings, roots, stems, cells, protoplasts. The parts of the plants as mentioned above are considered propagation material. The plant that is produced from the propagation material may comprise QTL1 that leads to resistance to the Bemisia tabaci species complex.

According to a further aspect thereof the invention provides a tissue culture of a plant carrying QTL1 of the invention, which is also propagation material. The tissue culture may comprise regenerable cells. Such tissue culture can be selected or derived from any part of the plant, in particular from leaves, pollen, embryos, cotyledon, hypocotyls, meristematic cells, roots, root tips, anthers, flowers, seeds, and stems. The tissue culture can be regenerated into a plant carrying QTL1 of the invention, which regenerated plant expresses the trait of the invention and is also part of the invention.

In one embodiment, the invention relates to a method for the production of a C. melo plant having QTL1 that leads to resistance to the Bemisia tabaci species complex, by using tissue culture of plant material that carries QTL1 in its genome.

The invention furthermore relates to a method for the production of a C. melo plant having QTL1 that leads to resistance to the Bemisia tabaci species complex, by using vegetative reproduction of plant material that carries QTL1 in its genome.

The invention furthermore relates to hybrid seed and to a method for producing such hybrid seed which may comprise crossing a first parent plant with a second parent plant and harvesting the resultant hybrid seed, wherein said first parent plant and/or said second parent plant has QTL1 of the invention. The resulting hybrid plant that may comprise QTL1 of the invention and which shows resistance to the Bemisia tabaci species complex is also a plant of the invention.

In one embodiment the plant of the invention which may comprise QTL1 of the invention either homozygously or heterozygously is a plant of an inbred line, a hybrid, a doubled haploid, or a plant of a segregating population.

The invention also relates to a method for the production of a C. melo plant having the QTL1 that leads to resistance to the Bemisia tabaci species complex, which method may comprise using a seed that may comprise QTL1 for growing the said C. melo plant. In one embodiment, the seeds are seeds of which a representative sample was deposited with the NCIMB under deposit number 42572.

In one embodiment, the invention relates to C. melo plants of the invention that carry QTL1 of the invention which leads to resistance to the Bemisia tabaci species complex, and that have acquired said QTL1 from a suitable source, either by conventional breeding, or genetic modification, in particular by cisgenesis or transgenesis. Cisgenesis is genetic modification of plants with a natural gene, coding for an (agricultural) trait, from the crop plant itself or from a sexually compatible donor plant. Transgenesis is genetic modification of a plant with a gene from a non-crossable species or a synthetic gene.

In one embodiment, the source from which QTL1 of the invention is acquired is formed by plants grown from seeds of which a representative sample was deposited under accession number NCIMB 42572, or from the deposited seeds NCIMB 42572, or from sexual or vegetative descendants thereof, or from another source which may comprise QTL1 as defined herein that leads to the resistance to the Bemisia tabaci species complex of the invention, or from a combination of these sources.

In a preferred embodiment, the invention relates to non-transgenic Cucumis melo plants. The source for acquiring QTL1 of the invention, to obtain a plant of the invention that has resistance to the Bemisia tabaci species complex, is suitably a Cucumis melo plant that carries the QTL1 as comprised homozygously in NCIMB 42572, or alternatively a plant of a Cucumis species that carries said QTL1 and that can be crossed with Cucumis melo. When a Cucumis species other than Cucumis melo is used as the source of QTL1 of the invention, optionally, techniques such as embryo rescue, backcrossing, or other techniques known to the skilled person can be performed to obtain seed of the interspecific cross, which seed can be used as the source for further development of a non-transgenic Cucumis melo plant that shows resistance to the Bemisia tabaci species complex.

To obtain QTL1 from a source in which it is heterozygously present, a seed of such plant can be grown and flowers can be pollinated with pollen from the same plant or from another plant that also has QTL1 heterozygously to obtain a fruit with seeds. When these seeds are sown, the resulting plants will segregate according to normal segregation ratios, which means that about 25% of the plants will have the QTL homozygously, about 50% will have the QTL heterozygously, and about 25% will not have the QTL. For selection of a preferred plant, having the QTL either homozygously or heterozygously, the presence of QTL1, can suitably be determined using the markers as described herein. Alternatively, plants can be phenotypically observed and visually selected for the presence of resistance to the Bemisia tabaci species complex. The skilled person is aware of how to work with QTLs in heterozygous and homozygous form using known breeding and selection procedures.

The invention also relates to the germplasm of plants of the invention. The germplasm is constituted by all inherited characteristics of an organism and according to the invention encompasses at least the trait of the invention. The germplasm can be used in a breeding programme for the development of C. melo plants having resistance to the Bemisia tabaci species complex. The use of the germplasm that may comprise QTL1 leading to resistance to the Bemisia tabaci species complex in breeding is also part of the present invention.

The invention also concerns the use of QTL1 leading to the trait of the invention for the development of C. melo plants that have resistance to the Bemisia tabaci species complex.

As used herein, a marker is genetically 'linked to' a QTL and can be used for identification of that QTL when the recombination between marker and QTL, i.e. between marker and trait, is less than 5% in a segregating population resulting from a cross between a plant which may comprise the QTL and a plant lacking the QTL.

In one embodiment the invention relates to a marker for identification of QTL1 which leads to resistance to the Bemisia tabaci species complex, which marker is selected from the group consisting of SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11 and SEQ ID No. 12.

In a preferred embodiment, the markers for identification are markers having SEQ ID No. 6, SEQ ID No. 7, SEQ ID No. 8, SEQ ID No. 9, SEQ ID No. 10, SEQ ID No. 11, SEQ ID No. 12. All markers can be used to develop other markers for the identification of QTL1.

According to a further aspect thereof, the invention relates to the use of a marker for identification of QTL1 which leads to resistance to the *Bemisia tabaci* species complex, which marker is selected from the group consisting of SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, and SEQ ID No. 12.

In a preferred embodiment, a marker selected from the group consisting of SEQ ID No. 6, SEQ ID No. 7, SEQ ID No. 8, SEQ ID No. 9, SEQ ID No. 10, SEQ ID No. 11, and SEQ ID No. 12 is used for identification of QTL1. In particular the marker having SEQ ID No. 11 is used for identification of QTL1.

In one aspect the invention relates to a method for the production of a *C. melo* plant that has resistance to the *Bemisia tabaci* species complex, which may comprise QTL1 that leads to resistance to the *Bemisia tabaci* species complex, which may comprise:

a) crossing a plant which may comprise QTL1, representative seed of which plant was deposited as NCIMB 42572, with a plant not which may comprise QTL1, to obtain an F1 population;

b) optionally performing one or more rounds of selfing and/or crossing a plant from the F1 to obtain a further generation population;

c) selecting a plant that may comprise QTL1 and has resistance to the *Bemisia tabaci* species complex, suitably by using a molecular marker linked to QTL1. The plant can also be phenotypically selected for having resistance to the *Bemisia tabaci* species complex.

The invention additionally provides a method of introducing another desired trait into a *C. melo* plant which may comprise resistance to the *Bemisia tabaci* species complex, which may comprise:

a) crossing a *C. melo* plant which may comprise QTL1 that leads to resistance to the *Bemisia tabaci* species complex, representative seed of which was deposited as NCIMB 42572, with a second *C. melo* plant that may comprise the other desired trait to produce F1 progeny;

b) selecting an F1 progeny that may comprise QTL1 and the other desired trait;

c) crossing the selected F1 progeny with either parent, to produce backcross progeny;

d) selecting backcross progeny which may comprise QTL1 and the other desired trait; and e) optionally repeating steps c) and d) one or more times in succession to produce selected fourth or higher backcross progeny that may comprise the other desired trait and has resistance to the *Bemisia tabaci* species complex. The invention includes a *C. melo* plant produced by this method and the *C. melo* fruit obtained therefrom.

Optionally selfing steps are performed after any of the crossing or backcrossing steps. Selection for a plant which may comprise QTL1 of the invention and the other desired trait can alternatively be done following any crossing or selfing step of the method.

The invention further provides a method for the production of a *C. melo* plant having resistance to the *Bemisia tabaci* species complex as defined herein by using a doubled haploid generation technique to generate a doubled haploid line that homozygously may comprise QTL1 that leads to resistance to the *Bemisia tabaci* species complex.

The invention also relates to a method for seed production which may comprise growing *C. melo* plants from seeds of the invention, allowing the plants to produce seeds, and harvesting those seeds. Production of the seeds is suitably done by crossing or selfing. Preferably, the seeds so produced have the capability to grow into plants that have resistance to the *Bemisia tabaci* species complex.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1: *Bemisia tabaci* Preference Test

*Cucumis melo* plants that were the result of internal research to identify new *C. melo* material with resistance to *Bemisia tabaci* were compared to other *C. melo* plants in a preference test performed in Spain. During this preference test, different *C. melo* accessions were placed together in a cage, and two such cages were used in the assessment as two repetitions. Next to susceptible controls, also some accessions known to have a level of resistance were included, to be used as resistant controls. The cages were inoculated with *B. tabaci* whiteflies, using several whitefly-infested eggplant leaves. The whiteflies were shaken off the leaves in the cages, and the leaves were subsequently pinned on stakes in the cages to make sure all whiteflies were deposited inside the cages.

Table 2 shows the material that was included in the test, and the observation scores. Scoring was done visually on three plants per accession on a scale of 1-5, whereby 1 is highly resistant, 2 is resistant, 3 is moderately resistant, 4 is susceptible, and 5 is highly susceptible. To assess a plant, the number of leaves that was infected was counted. Next to this a general assessment of the infection was done. Also, when relevant, the presence of sooty mold was taken into account. The combination of aspects then was given a score for the whole plant between 1 and 5.

Scoring was done at 4 weeks after inoculation (wai), and at 7 weeks after inoculation. Average results are presented in Table 2.

TABLE 2

| | Preference test | | | |
|---|---|---|---|---|
| Source | Cage 1 - 4 wai | Cage 1 - 7 wai | Cage 2 - 4 wai | Cage 2 - 7 wai |
| Vedrantais | 3.3 | 3 | 5 | 5 |
| Line 1 | 5 | 5 | 5 | 5 |
| TGR 1551 | 2 | 2 | 3.7 | 2.7 |
| PI 313970 | 3 | 3 | 2.8 | 2 |
| N11251 | 1 | 1 | 1 | 1 |

In this trial Vedrantais was used as the susceptible control. In addition an internally developed breeding line, Line 1, was included as comparison to confirm that the bio-assay is properly implemented and results in a good whitefly infection on susceptible material. Two publicly available *C. melo* sources, TGR 1551 and PI 313970, which is also known as 90625, that are mentioned in the art as having a certain level of *B. tabaci* resistance were included as resistant control.

N11251 is a plant resulting from the internal research to identify new *C. melo* sources with resistance to the *Bemisia tabaci* species complex.

The trial clearly showed in both repetitions that N11251 had a high level of resistance to whitefly in a preference test, which means the whiteflies can choose from different genotypes that are next to each other. The improvement in resistance over known sources was evident and resulted in the decision to do further research to identify the genetic background of this material, and to see how it would react in a no-choice test.

Example 2: *Bemisia tabaci* No-Choice Test

For the no-choice or non-preference test, *Bemisia tabaci* survival and reproduction were observed on plants of a single genotype that were placed in a greenhouse in the Netherlands. This experiment was done with whiteflies reared on a susceptible cucumber variety. Sowing of the experiment was done in March. For this experiment the whiteflies were placed in a so-called 'clipcage'. A clipcage is a type of small box that can be clipped on the leaf of an individual plant, and in which a number of insects can be placed. The insects can freely move within the box, but cannot escape and move to other leaves or other plants.

Figure 1:
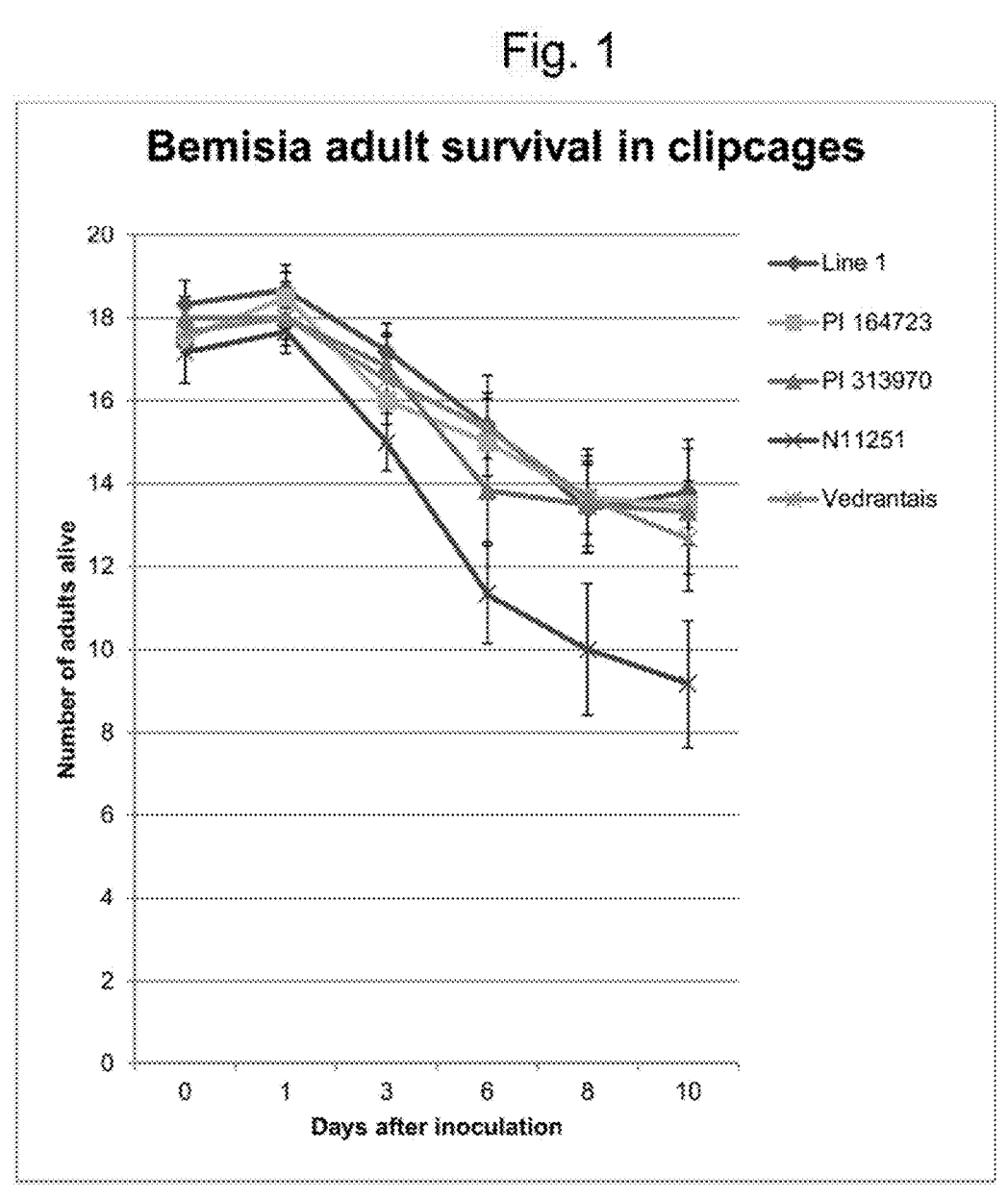

Again susceptible material and accessions that are known to have a level of resistance were included. Instead of TGR 1551, in this trial PI164723 was used. Six plants per genotype were observed, each of which had 1 clipcage. At three weeks after sowing the clip cages were placed on a well-developed leaf, and in each clipcage around 20 adult whiteflies were placed. Subsequently the number of surviving adult whiteflies was counted after 1, 3, 6, 8, and 10 days after inoculation (DAI). The results of the average number of adults of the six plants are presented in Table 3 and FIG. 1 containing standard errors.

TABLE 3

Adult survival rate in non-preference test average survival

| DAI | Line 1 | PI 164723 | PI 313970 | N11251 | Vedrantais |
|---|---|---|---|---|---|
| 0 | 18.3 | 17.5 | 18.0 | 17.2 | 17.7 |
| 1 | 18.7 | 18.5 | 18.0 | 17.7 | 18.0 |
| 3 | 17.2 | 16.0 | 16.8 | 15.0 | 16.5 |
| 6 | 15.4 | 15.0 | 13.8 | 11.3 | 15.3 |
| 8 | 13.4 | 13.7 | 13.5 | 10.0 | 13.7 |
| 10 | 13.8 | 13.5 | 13.3 | 9.2 | 12.7 |

The non-preference test again showed a good result for N11251, as the adult survival was clearly lower in this genotype when compared to susceptible material or material that is said to have a level of resistance. This indicates that N11251 does not only perform better in a free choice test, but also has an influence on the survival of the insects once they are forced to be on the plant. This is an important aspect for developing *C. melo* material that is useful in practice.

Next to the adult survival, also oviposition was observed for this material. In a similar set-up, and with the use of clipcages, again 20 whiteflies per plant were deposited on six plants of each genotype. The next day, 15 hours after inoculation, the clipcages and the whiteflies were removed. Three days after inoculation (3 DAI) the number of eggs was counted. Results of the average of six plants are presented in FIG. 2.

Again, it was clear that the material of the invention showed a far better resistance than the other accessions that were included in this test. The average number of eggs per plant of N11251 was a bit over 70, while the other four genotypes had between 120 and 130 eggs per plant after three days. From this it can be concluded that even if the same number of whiteflies is present, the offspring is much lower. The lower oviposition will likely result in a much slower population build-up, which reduces the whitefly incidence in the field and is therefore again a very important aspect of a useful resistance in practice.

Figure 3:
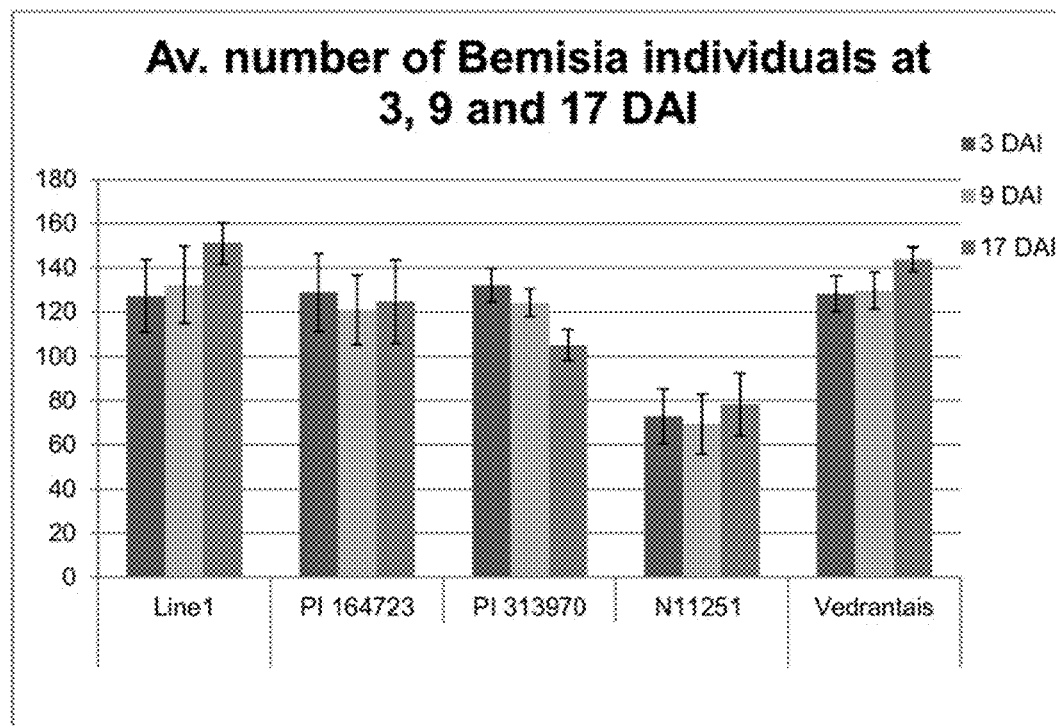
FIG. 3: life-cycle development on different *C. melo* accessions in a no-choice test.

The plants on which the eggs were deposited were again observed at 9 and 17 days after inoculation, and the total number of individuals of different stages was recorded, i.e. eggs, nymphs, pupae, and exuviae. Table 4 and FIG. 3 show the results as an average per plant.

TABLE 4 total Bemisia individuals
Average number of total individuals

| Genotype | 3 DAI | 9 DAI | 17 DAI |
|---|---|---|---|
| Line1 | 127 | 132 | 151 |
| PI 164723 | 129 | 121 | 125 |
| PI 313970 | 132 | 124 | 105 |
| N11251 | 73 | 69 | 78 |
| Vedrantais | 128 | 130 | 144 |

At 3 DAI all individuals are eggs, while at 9 DAI the counted number is totally build up by nymphs. It seems that there was not much variation in development from egg to nymph, as basically all eggs on all genotypes were advanced to the nymphal stage. The number sometimes goes slightly up since some eggs might be missed during the first count. This is the same between $2^{nd}$ and $3^{rd}$ count, whereby also some nymphs might have been miscounted.

The total number of individuals was significantly lower for N11251 at all observation days as compared to all other material that was included in this test.

Figure 4:
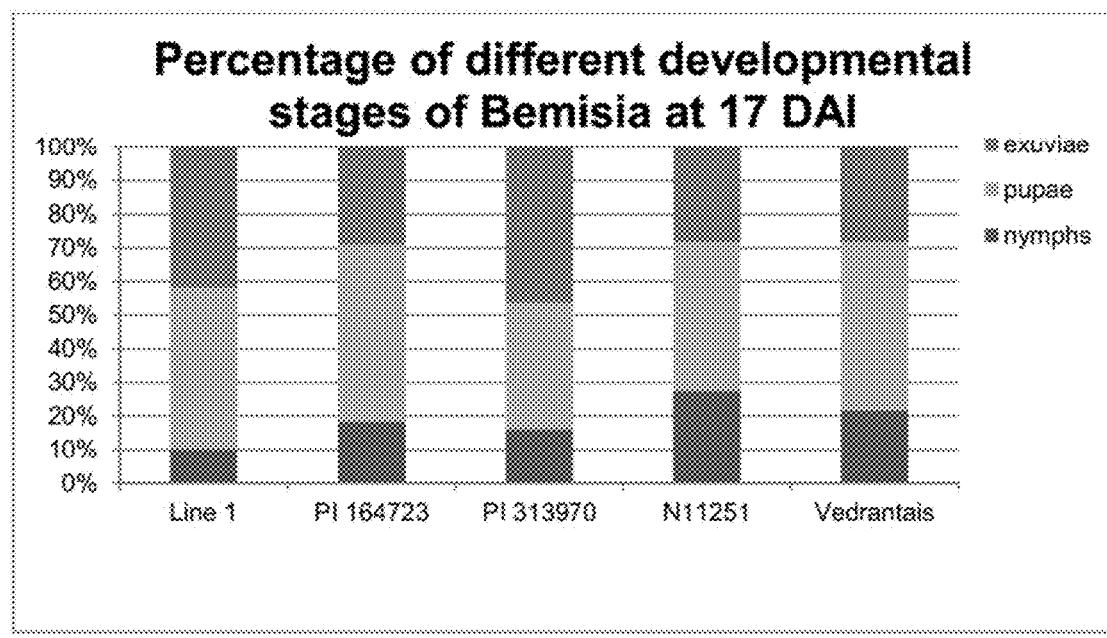
FIG. 4: population build-up on different *C. melo* accessions after a no-choice experiment, expressed as the percentage of the total per developmental stage.

As a last observation the population build-up regarding the different developmental stages that were present at 17 DAI was assessed. Results are presented in FIG. 4. The variation in population build-up is not that large, although it can be seen that Line 1 and PI313970 already have the largest percentage of exuviae, meaning new whiteflies have emerged, which indicates a fast life-cycle development. For N11251 the percentage that is still in nymphal stage was the highest among the material in this trial, as around 28% did not yet advance to the next stage. This indicates a slowdown in life-cycle development, which again contributes to a useful resistance mechanism in normal growing conditions.

Example 3: Mapping of QTL1

An F2 population resulting from a cross between Vedrantais and N11251 was used for QTL mapping of whitefly resistance. From the F2, 150 individual plants were phenotyped in a preference test for their resistance to whitefly, twice with a one week interval in between, on a scale of 1-5. In this trial, a score of 1 means completely susceptible, 2 is susceptible, 3 is moderately resistant, 4 is resistant, and a score of 5 is completely resistant. Five plants of each parent of the cross were also scored in the same way.

On the first assessment the average phenotypic score of Vedrantais was 2.8; one week later this was down to 1.0. The score of N11251 was 4.4 at the first observation, and 3.6 one week later. The average score over all F2 plants initially was 2.66; after one week the average score was 1.9.

All plants were sampled to obtain DNA. A large number of 887 markers were run on the samples. From these, 441 could be used for mapping as the others were non-polymorphic or otherwise non-informative. Each of the 441 markers got one of three scores per plant: AA for homozygous coming from Vedrantais, BB for homozygous resulting from N11251, and H for the heterozygotes.

Using JoinMap software, a linkage map was constructed from the genotypic data. To construct the map, first a maximum likelihood mapping approach was used to estimate the order of the markers per linkage group. After this, regression mapping was performed to predict the position of the markers per linkage group. Subsequently the Haldane mapping function was used to convert the recombination frequency into genetic distances in cM. In this way a good linkage map was obtained covering all 12 chromosomes of C. melo, with the lowest coverage for chromosome 10 which had only 10 markers, and the highest for chromosomes 4 and 11, each represented by 53 markers.

Mapping of the data resulted in the identification of a QTL on chromosome 4. A clear improvement in resistance over the publicly available sources was observed for this material (Examples 1 and 2). This QTL is further indicated as QTL1.

The markers that resulted from the QTL analysis as flanking the QTL1 on chromosome 4 are indicated with SEQ ID No. 1 and SEQ ID No. 2 (FIG. 5). In this population, SEQ ID No. 1 was mapped to position 24.4 cM, and SEQ ID No. 2 to position 0.0 cM, which indicates the QTL1 region. When these marker sequences were positioned on the present version of the publicly available C. melo genome map based on DHL92, the positions of the indicated SNPs were at 30.112.113 bp and 32.828.273 bp respectively. Therefore the position of the QTL1 of this invention in any other population can be deduced using this public genome map.

The mapping analysis of this population also resulted in the identification of a number of polymorphic SNP markers that can be used to predict the presence of the QTL1 on chromosome 4. The SNP markers resulting from mapping of this population are indicated with SEQ ID Nos. 3, 4, 5, 8, 9, 11, and 12 (FIG. 5). Table 1 shows the mapped position on chromosome 4 of these markers in the used population. In addition, these sequences were also positioned on the public genome map for C. melo in order to determine their actual physical location, as presented in Table 1. In this way these markers indicating the presence of the QTL1 on chromosome 4 can also be identified in any other population that has said QTL1.

Further developed C. melo material with QTL1 that leads to Bemisia resistance was subsequently also resequenced, and additional SNP markers were identified. These markers are indicated with SEQ ID Nos. 6, 7, and 10 in both Table 1 and FIG. 5. A C. melo plant that is part of the invention and may comprise QTL1 need not necessarily have all polymorphic SNP markers of SEQ ID Nos. 3-12, but the presence of one or more of said markers can be used to identify the presence of QTL1.

For all SNP markers Table 1 indicates the polymorphism present at the indicated position. The first nucleotide that is before the slash is as found in wild-type material, the second nucleotide after the slash indicates the SNP version that can be used for identification of the presence of QTL1.

The invention is further described by the following numbered paragraphs:

1. A Cucumis melo plant which carries QTL1 in its genome that leads to resistance against the Bemisia tabaci species complex, in particular to Bemisia tabaci biotype B and biotype Q, which QTL1 is located on chromosome 4 between flanking marker sequences SEQ ID No. 1 and SEQ ID No. 2.

2. A Cucumis melo plant of paragraph 1, wherein the QTL1 can be identified by one or more markers selected from the group consisting of SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, and SEQ ID No. 12, or combinations thereof.

3. A Cucumis melo plant of paragraph 1, wherein the QTL1 is linked to one or more markers selected from the group consisting of SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, and SEQ ID No. 12, or combinations thereof.

4. A Cucumis melo plant of paragraph 1, 2 or 3, which further comprises another Bemisia resistance conferring QTL, which combination of QTLs leads to an improved level of resistance to the Bemisia tabaci species complex when compared to a plant in which only the other QTL is present.

5. A Cucumis melo plant of paragraph 4, wherein the other Bemisia resistance conferring QTL is located on chromosome 11 and is as present in PI161375 and/or PI313970.

6. A Cucumis melo plant of any of the paragraphs 1-5, which Cucumis melo plant is resistant to the Bemisia tabaci species complex, in particular to Bemisia tabaci biotype B and biotype Q.

7. A Cucumis melo plant of any of the paragraphs 1-6, wherein the QTL1 is as comprised in the genome of a Cucumis melo plant representative seed of which was deposited with the NCIMB under deposit numbers NCIMB 42572.

8. A Cucumis melo plant of paragraph 7, wherein the QTL1 in the deposit is linked to one or more of the markers selected from the group consisting of SEQ ID No. 6, SEQ ID No. 8, SEQ ID No. 9, SEQ ID No. 10, SEQ ID No. 11, and SEQ ID No. 12, in particular by the marker having SEQ ID No. 11.

9. Propagation material suitable for producing a Cucumis melo plant of any one of the paragraphs 1-8, wherein the propagation material is suitable for sexual reproduction, and is in particular selected from microspores, pollen, ovaries, ovules, embryo sacs and egg cells, or is suitable for vegetative reproduction, and is in particular selected from cuttings, roots, stems, cells, protoplasts, or is suitable for tissue cultures of regenerable cells, and is in particular selected from leaves, pollen, embryos, cotyledon, hypocotyls, meristematic cells, roots, root tips, anthers, flowers, seeds and stems, and wherein the plant produced from the propagation material comprises QTL1 that leads to resistance to the Bemisia tabaci species complex, in particular to Bemisia tabaci biotype B and biotype Q.

10. Marker for the identification of QTL1, which when present on chromosome 4 in the genome of a Cucumis melo plant leads to resistance to the Bemisia tabaci species complex, in particular to Bemisia tabaci biotype B and biotype Q, which marker is selected from the group consisting of SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, and SEQ ID No. 12.

11. Marker of paragraph 10, which marker in the genome of a Cucumis melo plant that is resistant to the Bemisia tabaci species complex, in particular to Bemisia tabaci biotype B and biotype Q, as a result of the presence of QTL1, is located on chromosome 4.

12. Use of a marker of paragraph 10 or 11 for identification of QTL1 which when present in the genome of a *Cucumis melo* plant leads to resistance to the *Bemisia tabaci* species complex.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. An agronomically elite *Cucumis melo* plant having a QTL that leads to resistance against the *Bemisia tabaci* biotype B and biotype Q, wherein the QTL is located on chromosome 4 between flanking marker sequences SEQ ID NO: 1 and SEQ ID NO: 2, wherein the QTL is as comprised homozygously in the genome of a *Cucumis melo* plant, representative seed of which was deposited under NCIMB deposit number 42572, and wherein the QTL is introgressed into the plant.

2. The plant as claimed in claim 1, wherein the QTL is identified by one or more markers selected from the group consisting of SEQ ID NO: 3, SEQ ID NO: 4, SEQ ID NO: 5, SEQ ID NO: 6, SEQ ID NO: 8, SEQ ID NO: 9, SEQ ID NO: 10, SEQ ID NO: 11, and SEQ ID NO: 12, or combinations thereof.

3. The plant as claimed in claim 1, wherein the QTL is linked to one or more markers selected from the group consisting of SEQ ID NO: 3, SEQ ID NO: 4, SEQ ID NO: 5, SEQ ID NO: 6, SEQ ID NO: 8, SEQ ID NO: 9, SEQ ID NO: 10, SEQ ID NO: 11, and SEQ ID NO: 12, or combinations thereof.

4. The plant as claimed in claim 1, which further comprises another *Bemisia* resistance conferring QTL located on chromosome 11, and which combination of QTLs leads to an improved level of resistance to the *Bemisia tabaci* biotype B and biotype Q when compared to a plant in which only the QTL located on chromosome 11 is present.

5. The plant as claimed in claim 4, wherein the *Bemisia* resistance conferring QTL on chromosome 11 is as present in accession number PI161375 or accession number PI313970.

6. The plant as claimed in claim 1, wherein the introgressed QTL on chromosome 4 is linked to one or more of the markers selected from the group consisting of SEQ ID NO:6, SEQ ID NO: 8, SEQ ID NO: 9, SEQ ID NO: 10, SEQ ID NO: 11, and SEQ ID NO: 12.

7. A propagation material suitable for producing a *Cucumis melo* plant as claimed in claim 1,
wherein the propagation material is suitable for sexual reproduction, vegetative reproduction, or a tissue culture of regenerable cells, and
wherein the plant produced from the propagation material has the QTL that leads to resistance to *Bemisia tabaci* biotype B and biotype Q.

8. A method for selecting a *Cucumis melo* plant having an introgressing QTL that leads to resistance against *Bemisia tabaci* biotype B and biotype Q, said method comprising:
detecting in the plant or part thereof a marker selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 8, SEQ ID NO: 9, SEQ ID NO: 10, SEQ ID NO: 11, and SEQ ID NO: 12;
introgressing the QTL from the detected plant into another *Cucumis melo* plant by crossing; and selecting a *Cucumis melo* plant having the QTL; wherein the QTL leads to resistance against *Bemisia tabaci* biotype B and biotype Q.

9. The plant as claimed in claim 6, wherein the QTL in the deposit is linked to the marker having SEQ ID NO: 11.

10. The propagation material as claimed in claim 7, wherein the propagation material suitable for sexual reproduction is a microspore, pollen, ovary, ovule, embryo sac or egg cell.

11. The propagation material as claimed in claim 7, wherein the propagation material suitable for vegetative reproduction is a cutting, root, stem, cell or protoplast.

12. The propagation material as claimed in claim 7, wherein the propagation material suitable for the tissue culture of regenerable cells is a leaf, pollen, embryo, cotyledon, hypocotyl, meristematic cell, root, root tip, anther, flower, seed or stem.

* * * * *

SEQUENCE LISTING

```
<160> NUMBER OF SEQ ID NOS: 12

<210> SEQ ID NO 1
<211> LENGTH: 201
<212> TYPE: DNA
<213> ORGANISM: Cucumis melo

<400> SEQUENCE: 1
cagaaatatc tttctcgctg gcttgtgtaa taacttgttt caaccgatct tttgaagcct     60
aaatgaataa ttagggaagt gggaaatagt tgaaaaaaca aacgaaacca aaactcatat    120
agtgaataca gaattagatc aggaaaatgt tgctgcagtc tcacttttct gccatgygak    180
tctatgaaac atttttaatg g                                               201

<210> SEQ ID NO 2
<211> LENGTH: 201
<212> TYPE: DNA
<213> ORGANISM: Cucumis melo

<400> SEQUENCE: 2
tgctggacgt gaggtttcca tgartaagrt tctcctctgt gtggaggtag ttcaagcctt     60
gcgwgattcc gatcgcwatt ttcatccttg ttgcccaatc gaccgtggtt tctggcccac    120
gagctgcata cagtaaaaca aaagtaagta tatgagttay gagtatagyt taactagatc    180
aataacctct ttcataagta g                                               201

<210> SEQ ID NO 3
<211> LENGTH: 201
<212> TYPE: DNA
<213> ORGANISM: Cucumis melo

<400> SEQUENCE: 3
acagacccat ccatgatgtg aaaatactgc gggcatcagt taaagactaa agcttttcag     60
ttattgactt ttgacacact cgttgttgta tctcaacact gtatgcagca ataaaaacca    120
cgttgtgtgt ttsatgacag aaggaaggaa aggaaawgaa aattttccat gttagttagg    180
cgaagaaaga ggagggaaaa g                                               201

<210> SEQ ID NO 4
<211> LENGTH: 201
<212> TYPE: DNA
<213> ORGANISM: Cucumis melo

<400> SEQUENCE: 4
ctttggacga cggagatcgt cagccagaag gagagaacag agaggtcaca gagcagccgg     60
agattccgcc ggattttcca ccggaatcat tttggctctc gaaggatgca gagttcgatt    120
ggttagatca aaacgctttt tacgagagga aagattcgac gaaagggagt tcgaattcaa    180
cgaacttgaa tcctactgtg a                                               201

<210> SEQ ID NO 5
<211> LENGTH: 201
<212> TYPE: DNA
<213> ORGANISM: Cucumis melo
```

<400> SEQUENCE: 5

```
ttgggggaa ayagtgagtg tacgaycaaa gaatcaaaaa ggcttaaaca gacaaaatgt    60
ttgaaatggg acccaattga aatctgaccc ttgattgaga tggagaagat caacggatgg   120
ggtttgttca cacatggaga ataattccc actttccaca gtcaaaaaag gtcgaccacc    180
accgccacgg ttggagctgg a                                             201
```

<210> SEQ ID NO 6
<211> LENGTH: 201
<212> TYPE: DNA
<213> ORGANISM: Cucumis melo

<400> SEQUENCE: 6

```
taaggccaaa ggagttgata ctatcgcttg tatttcwgtc aatgatgcct ttgtgatgaa    60
ggcgtggaag gataacctta atatcaagga tgaggttctg ctrctgtctg atgggaatgg   120
ggatttcact agggctattg ggtgcgagct ggatttgagc gacaagcctg ttggaytggg   180
tgttaggtcg agacgttatg c                                             201
```

<210> SEQ ID NO 7
<211> LENGTH: 201
<212> TYPE: DNA
<213> ORGANISM: Cucumis melo

<400> SEQUENCE: 7

```
agagaaacra tagttaagta cctattgcct tcttcaactc ctcgaggtat ktaggctcta    60
acccatcgaa tgaattcata ataaaaccat aagaagcact gtcagcttta gccatttgat   120
tcccccactc caagaacaya ggatccaaag taaagataag ttgagacttg gtaacttgaa   180
tygratcagg aaaattaggg a                                             201
```

<210> SEQ ID NO 8
<211> LENGTH: 201
<212> TYPE: DNA
<213> ORGANISM: Cucumis melo

<400> SEQUENCE: 8

```
agtgtgattg acagaaaagt gtagcaatag aactggtaaa gaatcgcagt gcgagagtag    60
aaggaagaag ttgaacctag agcggtgcga aggccatcra cgtcgccrag ctgggaggcg   120
gwagctaggg ggcggaggtg aggggcgta tcggaatcga attcaataac accgtcctct   180
tcaaagagag cattgtcttc c                                             201
```

<210> SEQ ID NO 9
<211> LENGTH: 201
<212> TYPE: DNA
<213> ORGANISM: Cucumis melo

<400> SEQUENCE: 9

```
acttattaca ggaactcgat gggagatcac taagggtaaa ctatggacct ccaccgaaaa    60
gggacgattc ccctttcaga ggttctagaa atgcttcaag atttgacaac cgcaatcggg   120
tccatgtgag taaccttgct tggggtgttg acgatcttac acttgagaac ttgtttaggg   180
aacasggaaa tgttttggag g                                             201
```

<210> SEQ ID NO 10
<211> LENGTH: 201
<212> TYPE: DNA

```
<213> ORGANISM: Cucumis melo

<400> SEQUENCE: 10
tcgaaaattc aacccaaaaa ttaataaaag kagaacaaaa tccttactct gcacgcagaa      60
ccatatgttg gggcaacggg cccaaaacct tctccatcat ggcaagatgc tccaagttct     120
cgtgcgtttg aaaaagtgcc tcaccctgct catcaaacaa aagaaaataa caaaatggaa    180
aggttaagaa aatccakaac c                                              201

<210> SEQ ID NO 11
<211> LENGTH: 201
<212> TYPE: DNA
<213> ORGANISM: Cucumis melo

<400> SEQUENCE: 11
acgatgctga gtaaaaccag agggtgaact acaaccttct caactggcct cgatgaaatt      60
tgctgcgtct tgatcacatc catggcggaa tttttgcagt gtatcagagt tgaatcgaat    120
tggcgcttcc gtgctaargg ctaaacccac ttagaaatgg agcagctgct tattaagccc    180
yttttctttg agggttttc t                                               201

<210> SEQ ID NO 12
<211> LENGTH: 201
<212> TYPE: DNA
<213> ORGANISM: Cucumis melo

<400> SEQUENCE: 12
cgagctgggt tggaatgtay gtattgaaca cgttcgtggt ggcrtgggtt cttgtggttg      60
ggtttgggtt tggaggatgg gctagtatga cgaactttgt taggcaagta gacaccttcg    120
gacttttcgc aaagtgctat cagtgcaagg gtcccccgtt rcctgcgakg gctccaactg    180
ctcatcatta aactctgggc a                                              201
```